(12) United States Patent
Suzuki

(10) Patent No.: US 8,758,259 B2
(45) Date of Patent: Jun. 24, 2014

(54) APPARATUS AND METHOD FOR MEASURING PULSE WAVES

(75) Inventor: Takuji Suzuki, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 696 days.

(21) Appl. No.: 12/534,424

(22) Filed: Aug. 3, 2009

(65) Prior Publication Data

US 2010/0081947 A1    Apr. 1, 2010

(30) Foreign Application Priority Data

Sep. 26, 2008  (JP) .................... 2008-247445

(51) Int. Cl.
*A61B 5/02* (2006.01)

(52) U.S. Cl.
USPC ........................................... 600/500

(58) Field of Classification Search
USPC .................. 600/301, 509, 500–507
See application file for complete search history.

(56) References Cited

U.S. PATENT DOCUMENTS

| | | | |
|---|---|---|---|
| 7,381,188 B1* | 6/2008 | Farazi ............................ | 600/508 |
| 7,470,235 B2 | 12/2008 | Moriya et al. | |
| 2005/0234314 A1* | 10/2005 | Suzuki et al. ................ | 600/301 |
| 2008/0004811 A1 | 1/2008 | Suzuki et al. | |
| 2009/0018408 A1 | 1/2009 | Ouchi et al. | |
| 2009/0182239 A1 | 7/2009 | Ouchi et al. | |

FOREIGN PATENT DOCUMENTS

| | | |
|---|---|---|
| JP | 2001-070265 | 3/2001 |
| JP | 2004-121668 | 4/2004 |
| JP | 3635663 | 1/2005 |
| JP | 2007-117591 | 5/2007 |
| JP | 2007-125366 | 5/2007 |
| JP | 2007-181628 | 7/2007 |

OTHER PUBLICATIONS

"Traffic related pollution and heart rate variability in a panel of elderly subjects" by Schwartz et al., Thorax, vol. 60, pp. 455-461, 2004.*
Office Action in Japanese Patent Application No. 2008-247445, mailed Jan. 8, 2013 (with English translation).
U.S. Appl. No. 12/408,855, filed Mar. 23, 2009, Kazushige Ouchi et al.
U.S. Appl. No. 12/212,182, filed Sep. 17, 2008, Takuji Suzuki.

* cited by examiner

*Primary Examiner* — Patricia Mallari
*Assistant Examiner* — Vasuda Ramachandran
(74) *Attorney, Agent, or Firm* — Oblon, Spivak, McClelland, Maier & Neustadt, L.L.P.

(57) ABSTRACT

Pulse waves of a subject are detected in time sequence. Amplitude of the pulse waves is detected, and an interval between two pulse waves adjacent along a time axis is detected. A first change ratio of the interval along the time axis, and a second change ratio of the amplitude divided by the interval along the time axis are calculated respectively. By comparing the first change ratio and the second change ratio with a first threshold and a second threshold respectively, it is decided whether the pulse waves of the subject are irregular.

5 Claims, 11 Drawing Sheets

| DATA | PULSE WAVE AMPLITUDE | LOCAL MAXIMUM VALUE | RATIO |
|---|---|---|---|
| 1 | 624 | 0 | 0 |
| 2 | 416 | 140 | 0.336538 |
| 3 | 507.6 | 43 | 0.084712 |
| 4 | 281.9 | 45 | 0.159631 |
| 5 | 464 | 26 | 0.056034 |
| 6 | 618.1 | 184 | 0.297686 |
| 7 | 436.9 | 91 | 0.208286 |
| 8 | 343.6 | 127 | 0.369616 |
| 9 | 548.7 | 203 | 0.369965 |
| 10 | 510 | 158 | 0.309804 |
| 11 | 621 | 271 | 0.436393 |
| 12 | 252 | 120 | 0.47619 |
| 13 | 684 | 403 | 0.589181 |
| 14 | 822 | 524 | 0.63747 |
| 15 | 562 | 332 | 0.590747 |

FIG. 7

APPARATUS AND METHOD FOR MEASURING PULSE WAVES

CROSS-REFERENCE TO RELATED APPLICATIONS

This application is based upon and claims the benefit of priority from Japanese Patent Application No. 2008-247445, filed on Sep. 26, 2008; the entire contents of which are incorporated herein by reference.

FIELD OF THE INVENTION

The present invention relates to a method to measure a biological signal wave such as a subject's pulse wave.

BACKGROUND OF THE INVENTION

A waveform of a pulse or a heartbeat reflects the heartbeat, a status of blood vessel, or a status of autonomic nerve. Information having high accuracy (such as an electrocardiogram) is not acquired from this waveform, which is only used as an index to diagnose a disease. However, a method to diagnose using this waveform is easy for a doctor. Accordingly, by using a fluctuation or a shape of the waveform, a study to evaluate change of the human body has been made.

As a method for detecting the waveform, a photoelectric pulse wave sensor is usually used for monitoring the number of heartbeat during a person's exercise. The photoelectric pulse wave sensor irradiates a light into a living body, and a reflected light or a transmitted light from the living body is measured. In this case, the light is absorbed by haemoglobin in the living body, and an intensity of the reflected light or the transmitted light changes in proportion to a blood amount. Accordingly, a signal waveform synchronized with the heartbeat is observed as a pulse wave. As to the pulse wave, in comparison with another index (For example, the electrocardiogram) for the living body, a pulse wave sensor is easily wearable and suitable to use in daily life.

From the wave pulse, a blood flow pulsed from the heart and passed to the peripherals via the artery is observed. Accordingly, if a blood vessel system is regular (normal), a pulsation interval of the pulse wave is assumed to be equal to a pulsation interval of the heart (heartbeat interval), and the pulse wave interval is often used in the same way as R-R interval (heartbeat interval) of the electrocardiogram. In this case, by converting pulse wave interval data to a frequency spectrum distribution, a power spectrum at a low frequency region (LF: 0.05~0.15 Hz) and a high frequency region (HF: 0.15~0.4 Hz) is calculated from the frequency spectrum distribution (a sequence of the pulse wave interval data). Thus, an index of the autonomic nerve (used for deciding a sleep condition) is acquired from a value of the power spectrum.

However, in case of analyzing a frequency at the pulse wave interval, when an arrhythmia is mixed onto the pulse wave, the arrhythmia is observed as a noise having a spike shape, and a noise element overlaps with a wide band of the frequency region. Accordingly, in case of analyzing the frequency, the pulse wave interval data corresponding to the arrhythmia need be eliminated.

As a method for detecting the arrhythmia in the pulse wave, a minimum and a maximum are extracted from the pulse wave, and a difference between the minimum and the maximum is calculated as am amplitude. The amplitude larger than a threshold is decided as a signal, and the amplitude not larger than the threshold is decided as a noise (arrhythmia). This method is disclosed in "JP-A 2007-125366 . . . Reference 1".

Furthermore, as another method for detecting the arrhythmia, the arrhythmia itself is extracted from the pulse waveform observed, and used for diagnosis. This method is disclosed in "JP-A 2007-117591 . . . Reference 2" and "Japanese Patent No. 3635663 . . . Reference 3".

In the Reference 2, when pulse wave intervals largely distribute in a predetermined period, the arrhythmia is included in the pulse wave data, i.e., the condition of a patient is decided as the arrhythmia. In the Reference 3, by analyzing a frequency of pulse wave intervals in a predetermined period, from characteristic of distribution (fluctuation) of the frequency, the arrhythmia is decided to be included, i.e., the condition of a patient is decided as the arrhythmia.

As mentioned-above, in the Reference 1, the arrhythmia is decided by comparing the amplitude (calculated from the pulse wave) with the threshold. However, the pulse wave signal has the amplitude with fluctuation. Furthermore, the amplitude is not always small in case of the arrhythmia. Accordingly, the arrhythmia cannot be correctly detected.

In the Reference 2, the arrhythmia is decided by characteristic of distribution of pulse wave intervals. In the Reference 3, the arrhythmia is decided by analysis result of frequency of pulse wave intervals. In both cases, the arrhythmia cannot be decided for each pulse of the pulse waveforms. Briefly, in the References 1~3, the arrhythmia cannot be decided for each pulse by synthetically diagnosing the amplitude and the interval of pulse waveforms.

SUMMARY OF THE INVENTION

The present invention is directed to an apparatus and a method for deciding whether each waveform of the pulse wave is regular or arrhythmia.

According to an aspect of the present invention, there is provided an apparatus for measuring pulse waves, comprising: a pulse wave detection unit configured to detect pulse waves of a subject; an amplitude detection unit configured to detect an amplitude of the pulse waves; an interval detection unit configured to detect an interval between two pulse waves adjacent along a time axis; and a decision unit configured to calculate a first change ratio of the interval and a second change ratio of the amplitude divided by the interval along the time axis, and decide whether the pulse waves are irregular by comparing the first change ratio and the second change ratio with a first threshold and a second threshold respectively.

BRIEF DESCRIPTION OF THE DRAWINGS

FIG. 7 is a table showing pulse wave amplitude and a local maximum value of the pulse wave data.

DETAILED DESCRIPTION OF THE EMBODIMENTS

Figure 1:
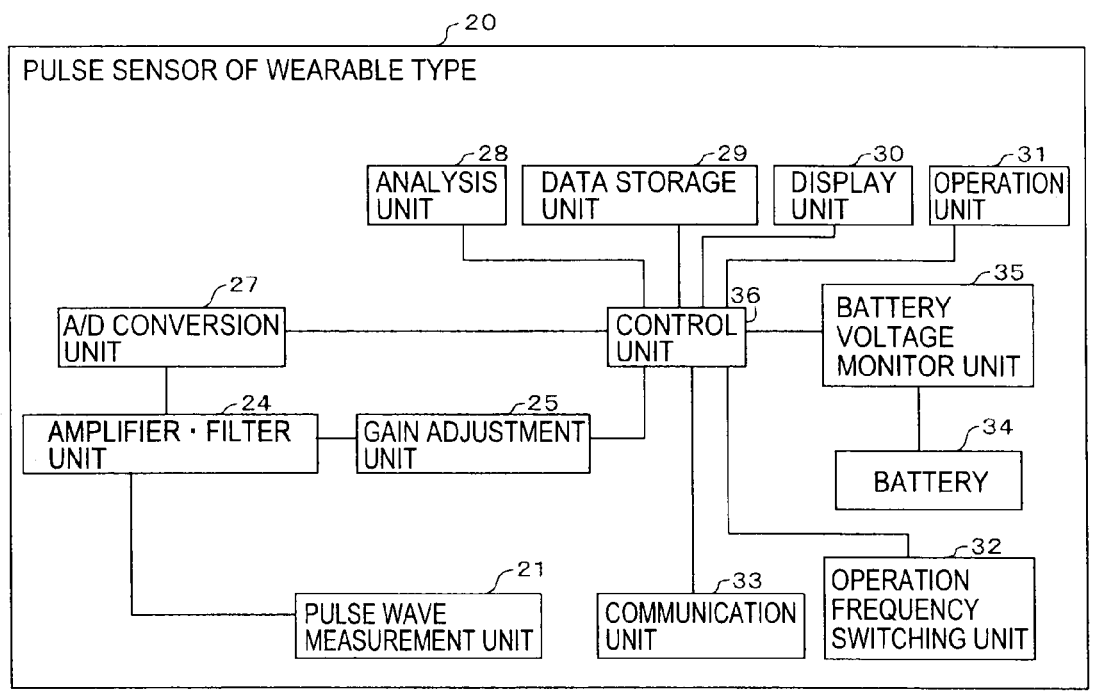
FIG. 1 is a block diagram of a pulse wave sensor of wearable type according to a first embodiment.

Hereinafter, embodiments of the present invention will be explained by referring to the drawings. The present invention is not limited to the following embodiments.

The First Embodiment

With regard to a measurement apparatus of the first embodiment, a sensor to detect a pulse wave as biological information of a subject (a user) calculates pulse wave interval data, and decides whether a pulse waveform of each pulse is the arrhythmia. Pulse wave interval data acquired from the pulse wave not decided as the arrhythmia are stored as regular data. On the other hand, another data are stored as arrhythmia data.

FIG. 1 is a block diagram of the measurement apparatus of the first embodiment. As the measurement apparatus, a pulse sensor 20 of wearable type is explained. Hereinafter, the pulse sensor of wearable type is called "a pulse sensor". First, component of the pulse sensor 20 is explained.

Figure 2:
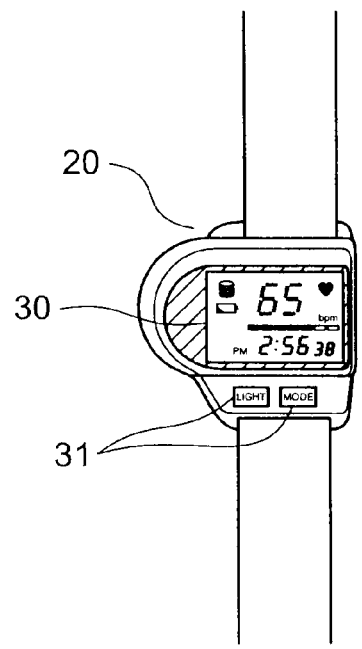
FIG. 2 is a schematic diagram of an appearance of the pulse wave sensor of wearable type.
Figure 3:
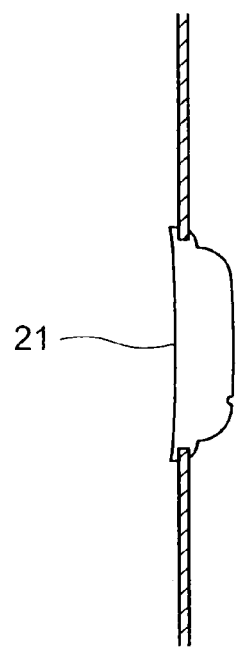
FIG. 3 is a schematic diagram of another appearance of the pulse wave sensor of wearable type.

FIGS. 2 and 3 show one example of appearance of the pulse sensor 20. FIG. 2 is a plan and FIG. 3 is a side view of the pulse sensor 20. The pulse sensor 20 has a shape worn by a wrist (such as a wristwatch). As shown in FIG. 2, a display unit 30 and an operation unit 31 are equipped on the surface of the pulse sensor 20. Furthermore, as shown in FIG. 3, a pulse wave measurement unit 21 to detect the subject's wave pulse is equipped on the under surface of the pulse sensor 20.

FIG. 1 is a block diagram of component of the pulse sensor 20 of the first embodiment. As shown in FIG. 1, the pulse sensor 20 includes the pulse wave measurement unit 21 (pulse wave detection means), an amplifier•filter unit 24, a gain adjustment unit 25, an A/D (analog/digital) conversion unit 27, an analysis unit 28, a data storage unit 29, the display unit 30, the operation unit 31, an operation frequency switching unit 32, a communication unit 33, a battery 34, a battery voltage monitor unit 35, and a control unit 36.

As shown in FIG. 3, the pulse wave measurement unit 21 measures a pulse wave on the under surface of the pulse sensor 20. The pulse wave measurement unit equips a green color LED and a photo diode. The green color LED radiates a light onto a skin surface of the wrist, and the photo diode detects the reflected light changed by the blood flow in the capillary vessel.

The amplifier•filter unit 24 amplifies and filters a pulse waveform measured. With regard to the amplifier•filter unit 24, a current/voltage converter converts an output current (from the photo diode of the pulse wave measurement unit 21) to a voltage, an amplifier amplifies the voltage, and filter processing is executed using a high-pass filter (For example, cutoff frequency: 0.1 Hz) and a low-pass filter (For example, cutoff frequency: 50 Hz).

The gain adjustment unit 25 adjusts an amplification ratio of the amplifier•filter unit 24 based on the measurement status. Concretely, the gain adjustment unit 25 calculates an amplitude of the pulse waveform (input to the control unit 36), and controls the amplification ratio of the amplifier•filter unit 24 by comparing the amplitude with a threshold.

The A/D conversion unit 27 executes A/D conversion of output from the pulse wave measurement unit 21. The analysis unit 28 analyzes data acquitted by the A/D conversion unit 27. The analysis unit 28 includes a pulse wave detector to detect a pulse wave of the subject, an amplitude detector to detect an amplitude of the pulse wave, an interval detector to detect an interval of the pulse wave, a product calculator to calculate the product of the amplitude and the interval and/or a ratio calculator to calculate a ratio of the amplitude to the interval, and a comparator to compare the product and/or the ratio with respective threshold.

Concretely, the analysis unit 28 analyzes the pulse waveform (measured by the pulse wave measurement unit 21, amplified/filtered by the amplifier•filter unit 24, and A/D converted by the A/D conversion unit 27), and calculates pulse wave interval data.

The data storage unit 29 (such as a flash memory) stores measurement data (such as pulse wave interval data) as an analysis result from the analysis unit 28. Concretely, the data storage unit 29 is a flash memory.

The display unit 30 is an apparatus for displaying a time, the number of pulse, a measurement status of pulse wave, a battery status, a memory status, and a communication status. Concretely, the display unit 30 is a LCD (Liquid Crystal Display).

The operation unit 31 equips a switch to change mode (a time mode, a measurement mode), and a push switch to turn on a backlight. The operation frequency switching unit 32 switches an operation frequency based on the mode (set by the operation unit 31). In case of the time mode, the power consumption is reduced by minimizing the operation frequency necessary for time-control.

The communication unit 33 transmits/receives data with an external apparatus. For example, the communication unit 33 transmits data (stored in the data storage unit 29) to an apparatus for measuring autonomic nerve index (not shown in Fig.). The communication unit 33 executes data communication with the external apparatus such as a PC, a PDA terminal or a cellular-phone. Concretely, the communication unit 33 is composed by USB. For example, pulse wave data at sleeping time in a plurality of days are measured. By connecting a USB port of the PC, the pulse wave data (having a format analyzable by predetermined analysis software) are stored into a hard disk of the PC. As a result, the pulse wave data can be analyzed by the analysis software.

The battery 34 supplies a power to all the pulse sensor 20. The battery voltage monitor unit 35 monitors a voltage of the battery 34. The control unit 36 controls the pulse sensor 20. In response to a request and an indication from the subject (user), the control unit 36 controls processing request and data flow for each unit. Concretely, by receiving the subject's request, the control unit 36 controls ON/OFF of the power supply and each processing to start/execute measurement.

Figure 4:
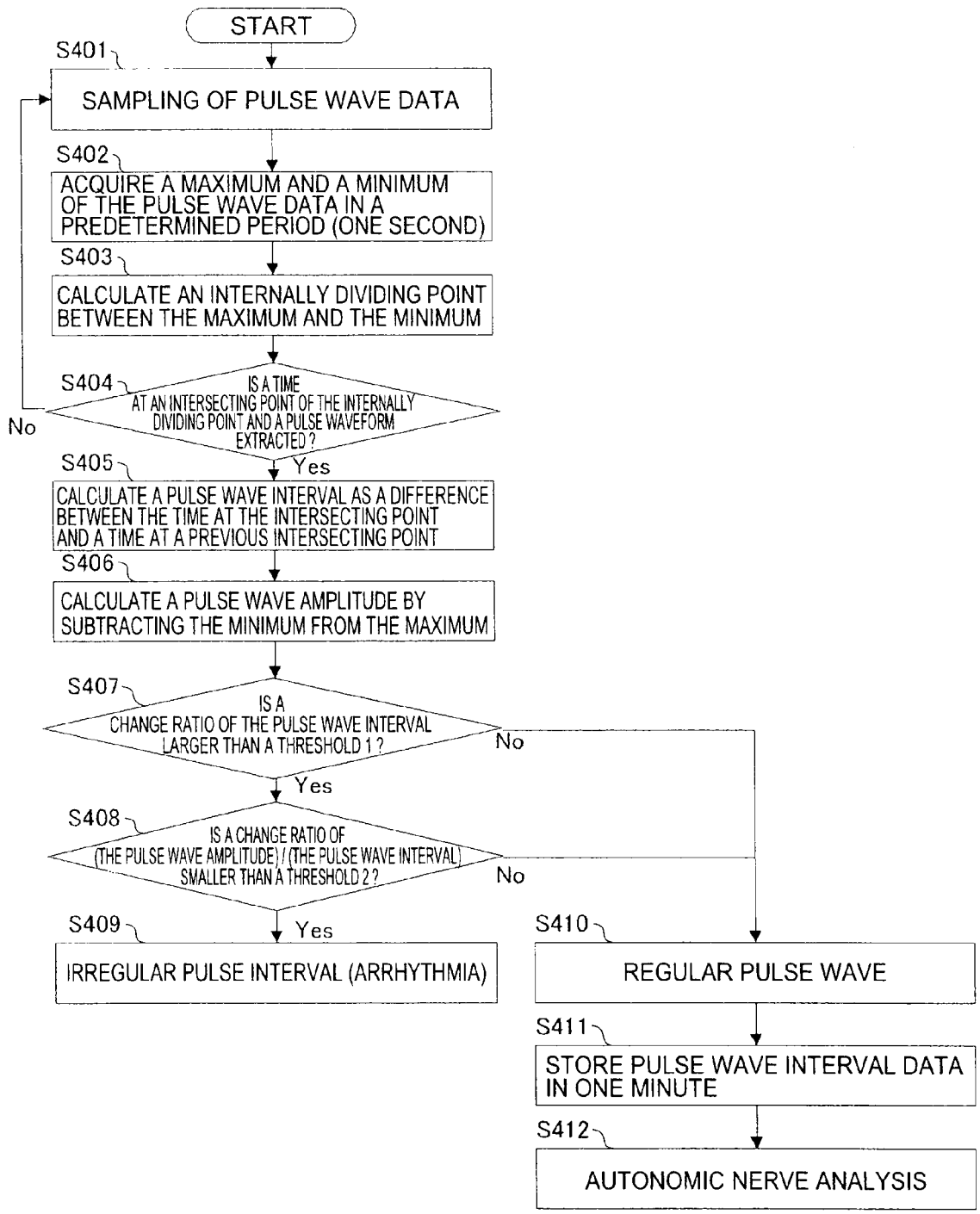
FIG. 4 is a flow chart of processing to calculate a pulse wave interval according to the first embodiment.

Next, processing to calculate a pulse wave interval by the pulse sensor 20 is explained by referring to FIG. 4. First, the analysis unit 28 executes sampling of pulse wave data (S401). As to each sampling point of the pulse wave data, the analysis unit 28 acquires a maximum and a minimum from the pulse wave data in approximately one second period centering the sampling point (S402).

Figure 5A:
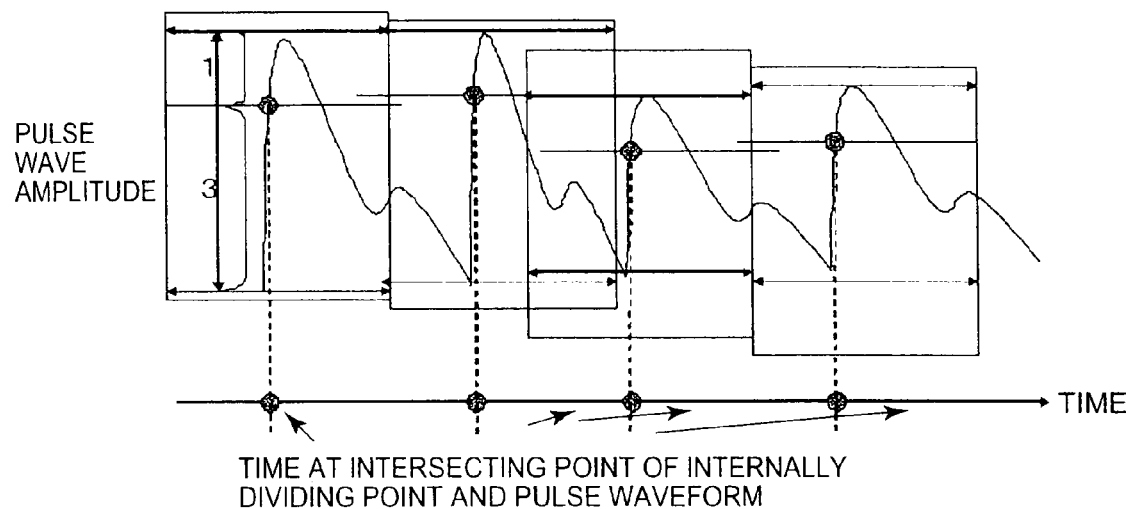
FIGS. 5A and 5B are schematic diagrams showing calculation processing of pulse wave interval data.

Next, the analysis unit 28 calculates an internally dividing point (a standard value) between the maximum and the minimum (S403). For example, the analysis unit 28 calculates a difference between the maximum and the minimum, and calculates the internally dividing point of the difference (For example, 3:1) as the standard point as shown in FIG. 5A.

Figure 5B:
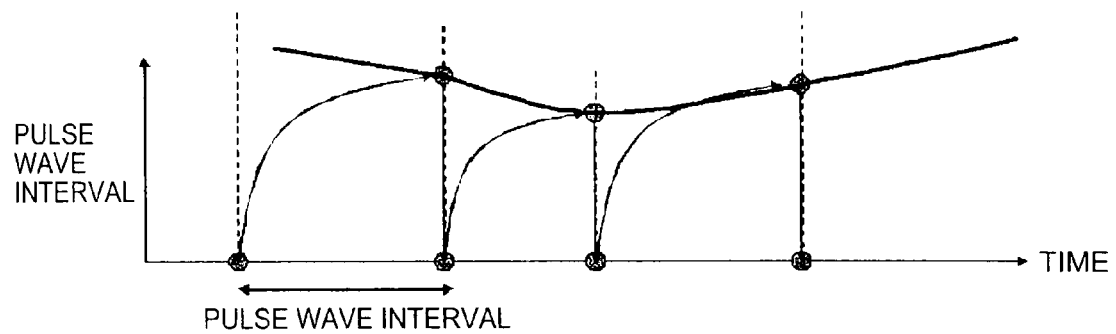

Next, from a series of pulse wave data the analysis unit 28 from which change element of direct current was eliminated, the analysis unit 28 calculates a time at an intersecting point between the standard point and the pulse waveform as shown in FIG. 5B, and calculates a time interval between the time and a time at a previous intersecting point (between a previous standard point and a previous waveform) as pulse wave interval data (S405). Next, the analysis unit 28 calculates a pulse wave amplitude by subtracting the minimum from the maximum (S406). The pulse wave interval data and the pulse wave amplitude each corresponding to the same time are stored in the data storage unit 29.

Next, as to the pulse wave interval, the case that a change ratio of the pulse wave interval to a previous pulse wave interval is larger than a threshold 1 (For example, 0.1) is detected (S407). For example, a change ratio 1 is calculated as follows.

Change ratio 1=|{(previous pulse wave interval)− (present pulse wave interval)}/(previous pulse wave interval)|

Next, when the change ratio 1 is larger than the threshold 1, the pulse wave amplitude is divided by the pulse wave interval. A change ratio 2 of (the pulse wave amplitude)/(the pulse wave interval) is calculated, and the case that the change ratio 2 is smaller than a threshold 2 (For example, 0.1) is detected (S408). For example, the change ratio 2 is calculated as follows.

$$\text{Change ratio 2} = \frac{\left|\left\{\frac{\text{(previous pulse wave amplitude)}}{\text{(previous pulse wave interval)}}\right\} - \left\{\frac{\text{(present pulse wave amplitude)}}{\text{(present pulse wave interval)}}\right\}\right|}{\frac{\text{(previous pulse wave amplitude)}}{\text{(previous pulse wave interval)}}}$$

When the change ratio is smaller than the threshold 2, the pulse wave interval is decided as an irregular pulse interval (arrhythmia) (S409). In other cases, the pulse wave is decided as a regular pulse wave (S410). As to the threshold 1; and 2, by acquiring pulse wave data of each subject in a rest, a standard deviation may be used as the threshold. Next, the analysis unit 28 stores the pulse wave interval data (decided as the regular pulse wave) in one minute (S411), and executes autonomic nerve analysis of this data set (S412).

Figure 6A:
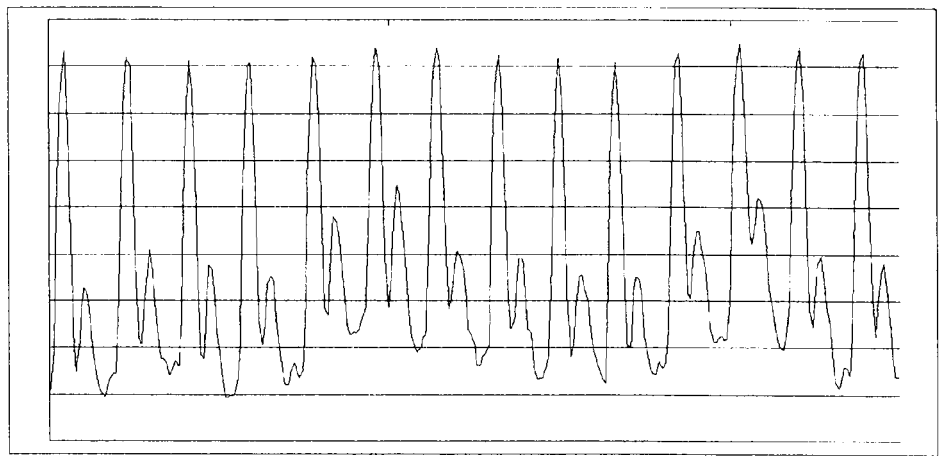
FIGS. 6A and 6B are schematic diagrams of pulse wave data, a differential waveform, a maximum, a minimum, and an internally dividing point thereof.
Figure 6B:
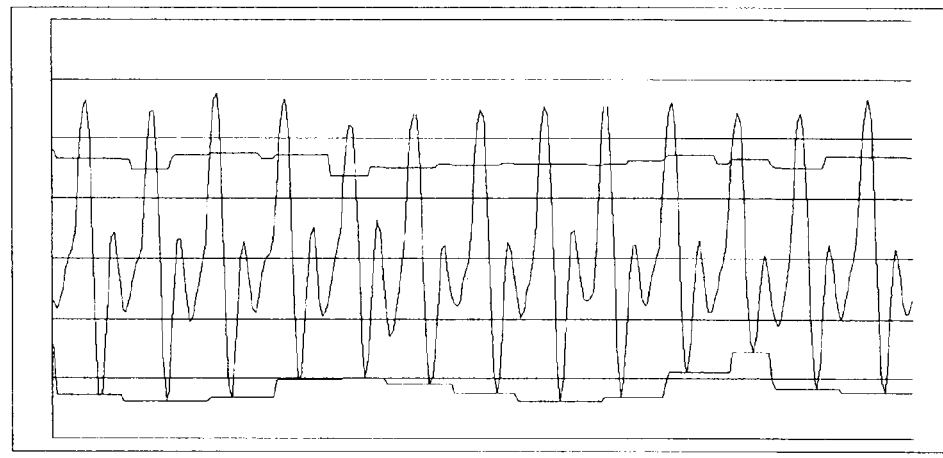

As to a ratio to set the internally dividing point, in order to correctly detect an interval of each pulse wave, a suitable range of the ratio exists. In general, the pulse waveform is different by a status of the blood vessel or the movement circulation of the blood of the subject. In case of the blood vessel having a large elasticity, as shown in FIG. 6A, the latter half of the waveform has a small local maximum value. A base line of the pulse waveform has fluctuation, and time-differentiation is subjected to the pulse waveform to eliminate the fluctuation. In this case, as shown in FIG. 6B, a part of the local maximum value is emphasized and appears at a center (mid point between the maximum and the minimum) in a range of differentiated pulse waveform approximately. Accordingly, the standard point (internally dividing point) need be set in larger value side (upper side) than the local maximum value.

FIG. 7 is a table that the pulse wave amplitude, the local maximum value, and a ratio thereof are experimentally measured for fifteen subjects (age: 20~64). In this table, the largest ratio is 0.637 (data 14). As a result, by setting the internally dividing point to a ratio above 0.64 (64:36 per 100), the local maximum value is prevented from erroneously selected.

Before the pulse sensor is used regularly, by acquiring the largest ratio of the local maximum value from test data, a predetermined margin may be added to the largest ratio. For example, if the largest ratio of the local maximum value is 0.5, a ratio of the internally dividing point is set as 0.6 by adding the margin 0.1.

In above explanation, in order to compare with the threshold 1, a change rate of the pulse width interval is used. However, a change rate of the product of the pulse wave interval and the pulse wave amplitude may be used.

Figure 8:
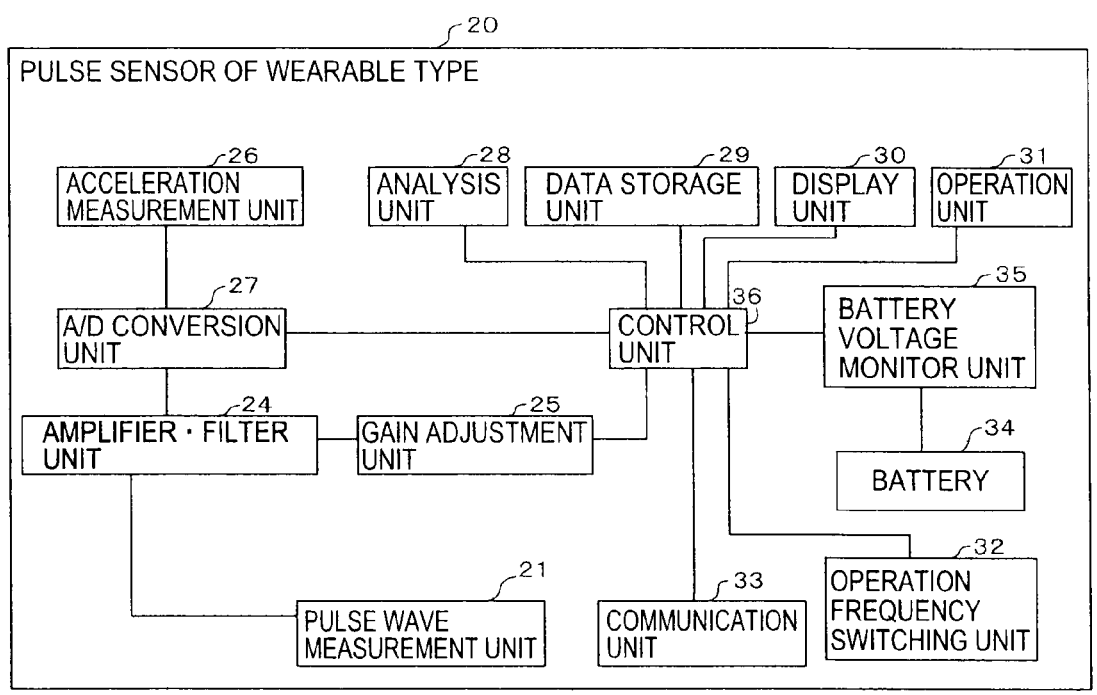
FIG. 8 is a block diagram of the pulse wave sensor of wearable type according to a modification of the first embodiment.

Furthermore, as shown in FIG. 8, an acceleration measurement unit 26 may be added into the pulse sensor 20. At the same time when the pulse wave is measured, the acceleration measurement unit 26 measures body motion data of a subject, and decides whether the subject has a body motion before deciding the arrhythmia. When the subject has the body motion, the pulse wave interval is eliminated because of a fluctuation by the body motion. When the subject does not have the body motion, the pulse interval data not decided as the arrhythmia are used as regular pulse data. As a result, accuracy to measure the pulse wave interval further rises.

Figure 9:
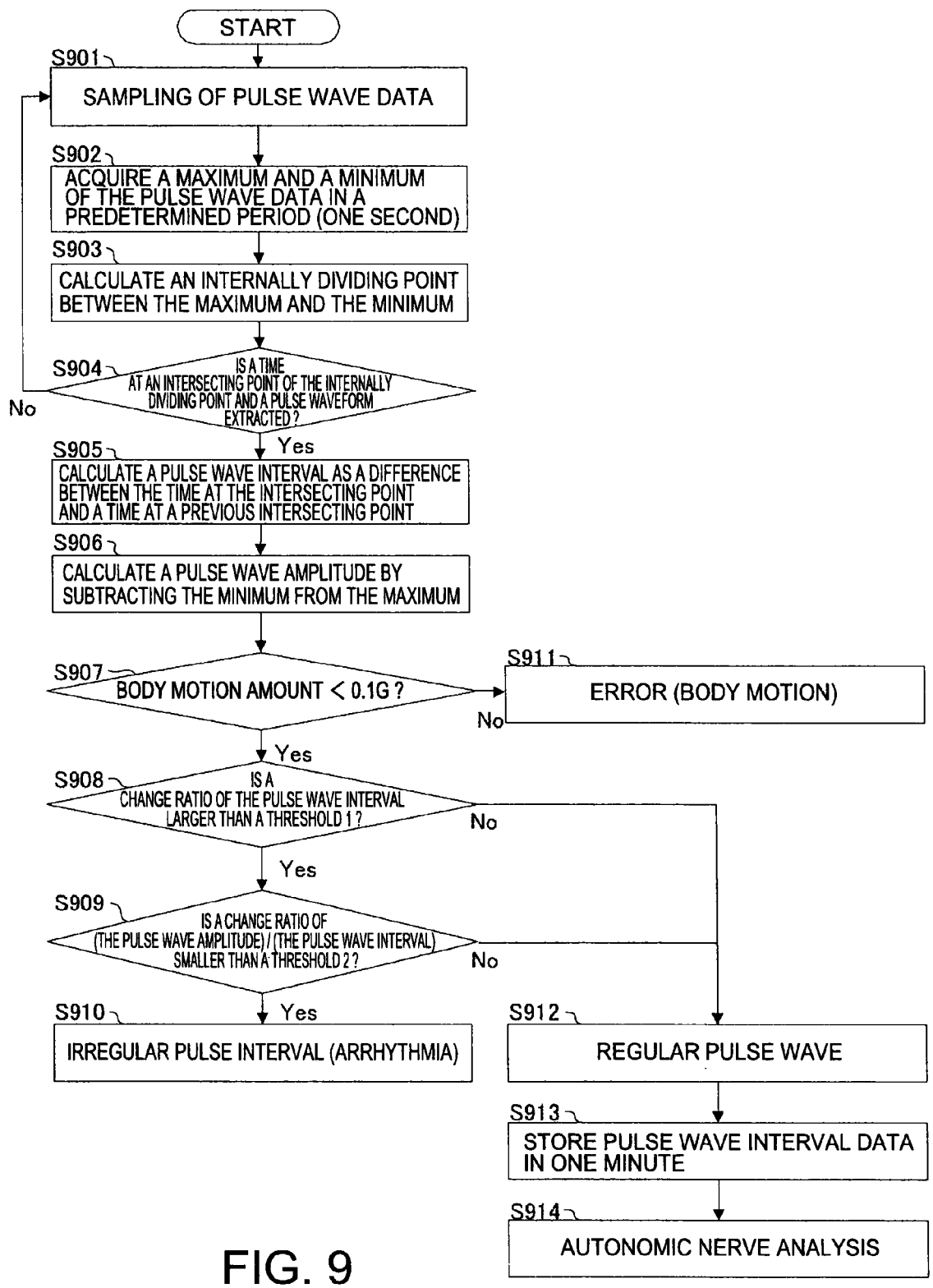
FIG. 9 is a flow chart of processing to calculate a pulse wave interval according to the modification of the first embodiment.

As shown in a flow chart of FIG. 9, a body motion amount is measured in a predetermined period (For example, 0.3 second) including timing to detect the pulse wave interval, the pulse wave amplitude and the intersecting point. Concretely, acceleration values along three axes XYZ are sampled, a change amount between sampled values is calculated, and a square root of the square sum of the change amount is calculated. A time average or a maximum value of the square root is set as the body motion amount. If the body motion amount is larger than 0.1 G, the pulse wave interval is affected by the body motion, and the interval data is decided as error data (S907, S911). In other cases, in the same way as FIG. 4, the pulse wave interval is decided whether to be irregular (arrhythmia).

Figure 10:
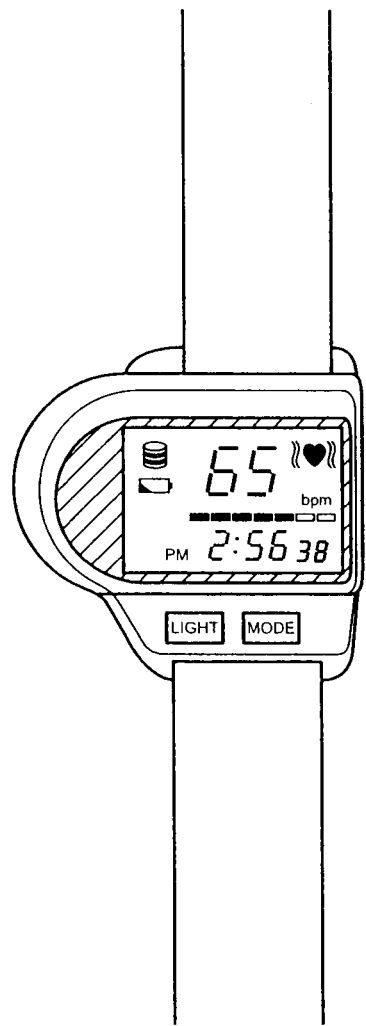
FIG. 10 is one example of the pulse wave sensor showing a detection of arrhythmia.

In above explanation, in case of autonomic nerve analysis, the present method is applied to eliminate the pulse wave interval having the arrhythmia from pulse wave interval data. However, in case of detecting the arrhythmia, the decision result is output on a display unit of the pulse sensor 20. For example, as shown in FIG. 10, while a heart mark is blinking in synchronization with the pulse, in case of detecting the arrhythmia, a wave line is displayed on both sides of the heart mark to inform the arrhythmia. Alternatively, at a completion time of measurement, the number (or a time average) of arrhythmia occurred in a period from a start time to the completion time is displayed. Furthermore, by transmitting this data to a PC via the communication unit 33, the PC may display the number (or the time average) of arrhythmia.

The Second Embodiment

In the first embodiment, the pulse sensor 20 having the pulse wave sensor 21 and the acceleration sensor 26 is explained. On the other hand, in the measurement apparatus of the second embodiment, instead of the pulse sensor 20, a mat sensor detecting a heartbeat and a body motion is explained. Briefly, in the second embodiment, a mat sensor as a sensor module of mat type is used. By measuring a vibration of the breast or the belly of a subject, the heartbeat and the body motion is detected during the subject is sleeping.

Figure 11:
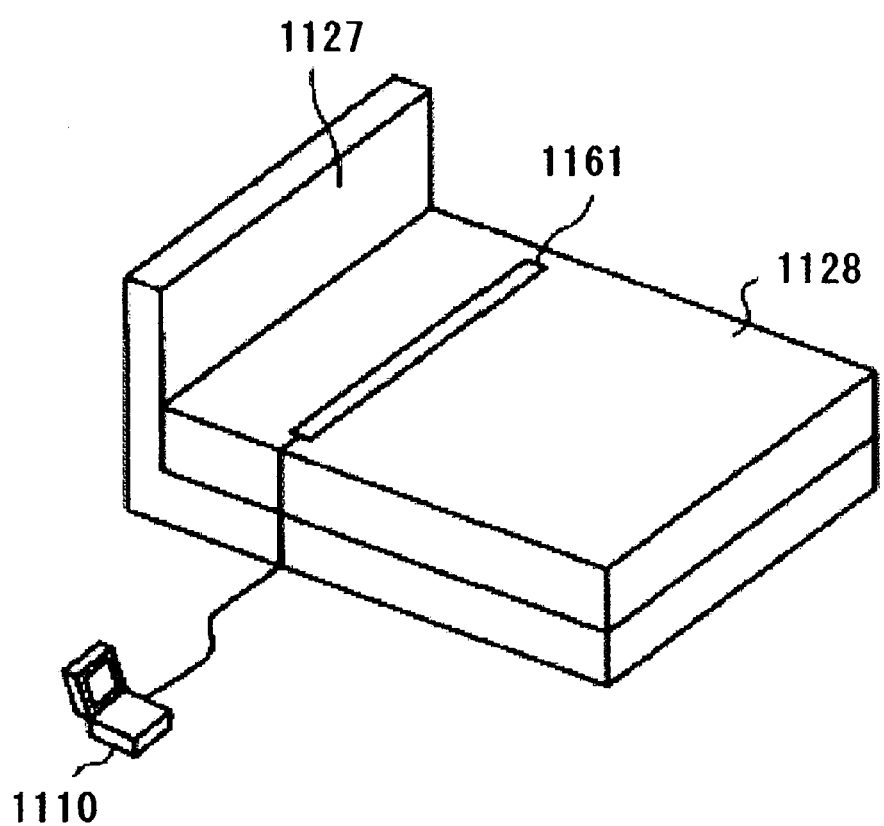
FIG. 11 is a schematic diagram of location example of a mat sensor according to a second embodiment.

FIG. 11 is a schematic diagram of location example of the mat sensor. The mat sensor is connected to a pressure measurement unit 1161 located on the surface of a mattress 1128 of a bed 1127.

The pressure measurement unit 1161 detects non-existence, existence on the bed, and body motion of the subject. The pressure measurement unit 1161 is located at a position corresponding to the subject's breast or belly, and measures the vibration by the subject's motion. The heartbeat and the body motion are detected from this measurement result. Briefly, in the second embodiment, instead of the pulse wave measurement unit 21 and the acceleration measurement unit 26, the pressure measurement unit 1161 is equipped.

The pressure measurement unit 1161 is formed with a macromolecule piezoelectric material such as a polyvinylidene fluoride. This is a piezoelectric element that a flexible electrode film is adhered as a tape shape on both surfaces of the polyvinylidene fluoride formed as a thin film.

Figure 12:
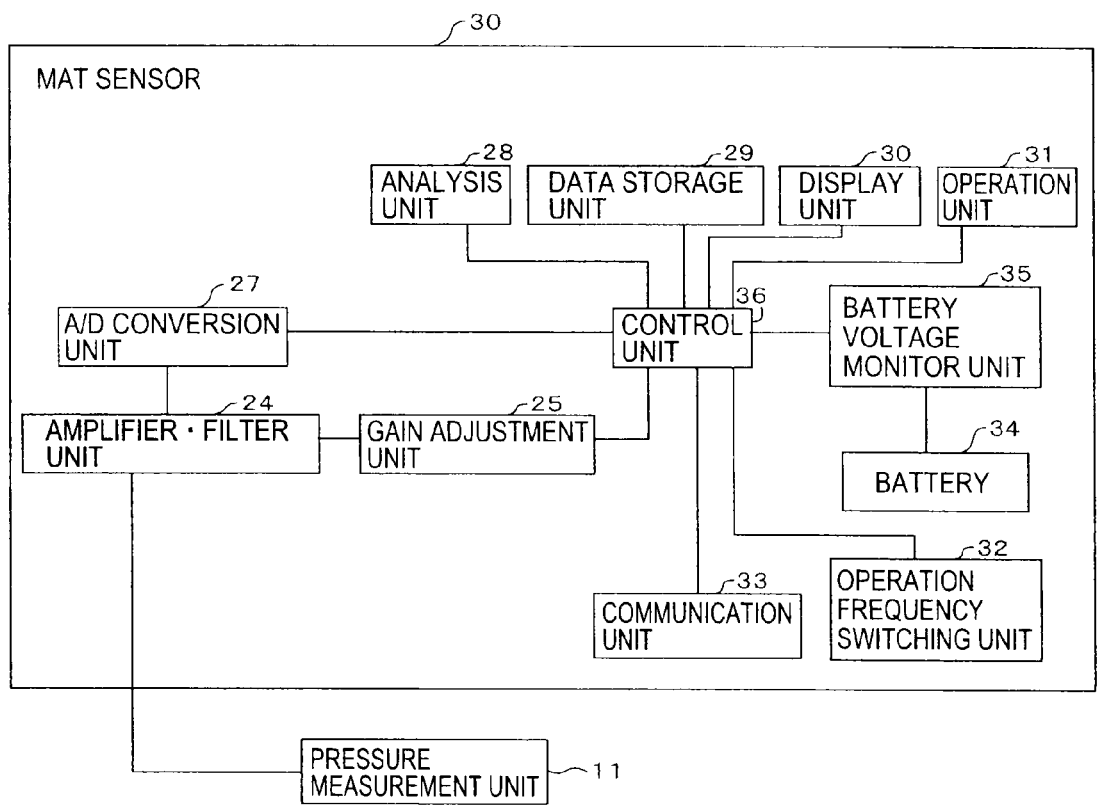
FIG. 12 is a block diagram of the mat sensor according to the second embodiment.

FIG. 12 is a block diagram of the mat sensor 30 of the second embodiment. The mat sensor 30 includes the amplifier•filter unit 24, the gain adjustment unit 25, the A/D conversion unit 27, the analysis unit 28, the data storage unit 29, the display unit 30, the operation unit 31, the operation frequency switching unit 32, the communication unit 33, the battery 34, the battery voltage monitor unit 35, and the control unit 36.

In the second embodiment compared with the first embodiment, the pulse wave measurement unit 21 and the acceleration measurement unit 26 are removed, the pressure measurement unit 11 is connected to the amplifier•filter unit 24, and the amplifier•filter unit has different function. Other units and functions in FIG. 12 are same as the pulse sensor 20 of the first embodiment in FIG. 1. Accordingly, the same sign is assigned to the other units in FIG. 12 and the explanation is omitted.

The amplifier•filter unit 24 separates an output of the pressure measurement unit 11 to a heartbeat element and a body motion element respectively, and outputs these elements to the A/D conversion unit 27. As a filter, a suitable one for the band to measure the heartbeat and the body motion is used.

As mentioned-above, in the measurement apparatus of the second embodiment, instead of pulse wave measurement, the heartbeat is measured. As to the heartbeat measured, processing for the pulse wave is executed in the same way as the first embodiment. Other components and processing are same as the first embodiment, and the explanation is omitted.

In this way, in the second embodiment, the measurement apparatus has a component using the mat sensor. Accordingly, measurement of the pulse wave interval, and detection of the arrhythmia, can be realized without restricting the subject's body.

As mentioned-above, with regard to the present invention, the measurement apparatus is easily used for the subject in daily life as the pulse sensor or the mat sensor. By removing a pulse wave interval having the arrhythmia previously, the pulse wave interval data of the subject is stably evaluated for the autonomic nerve analysis. Furthermore, possibility that the arrhythmia occurs is early detected for the subject in daily life.

In the disclosed embodiments, the processing can be performed by a computer program stored in a computer-readable medium.

In the embodiments, the computer readable medium may be, for example, a magnetic disk, a flexible disk, a hard disk, an optical disk (e.g., CD-ROM, CD-R, DVD), an optical magnetic disk (e.g., MD). However, any computer readable medium, which is configured to store a computer program for causing a computer to perform the processing described above, may be used.

Furthermore, based on an indication of the program installed from the memory device to the computer, OS (operation system) operating on the computer, or MW (middle ware software), such as database management software or network, may execute one part of each processing to realize the embodiments.

Furthermore, the memory device is not limited to a device independent from the computer. By downloading a program transmitted through a LAN or the Internet, a memory device in which the program is stored is included. Furthermore, the memory device is not limited to one. In the case that the processing of the embodiments is executed by a plurality of memory devices, a plurality of memory devices may be included in the memory device.

A computer may execute each processing stage of the embodiments according to the program stored in the memory device. The computer may be one apparatus such as a personal computer or a system in which a plurality of processing apparatuses are connected through a network. Furthermore, the computer is not limited to a personal computer. Those skilled in the art will appreciate that a computer includes a processing unit in an information processor, a microcomputer, and so on. In short, the equipment and the apparatus that can execute the functions in embodiments using the program are generally called the computer.

Other embodiments of the invention will be apparent to those skilled in the art from consideration of the specification and embodiments of the invention disclosed herein. It is intended that the specification and embodiments be considered as exemplary only, with the scope and spirit of the invention being indicated by the claims.

What is claimed is:
1. An apparatus for measuring pulse waves, comprising:
a pulse wave detection unit configured to detect pulse waves of a subject;
an amplitude detection unit configured to detect a plurality of amplitudes of the pulse waves;
an interval detection unit configured to detect an interval of time between two of the pulse waves, the two being adjacent along a time axis; and
a decision unit configured to calculate a first change ratio and a second change ratio, compare the first change ratio with a first threshold, and, when the first change ratio is larger than the first threshold, decide whether the pulse waves represent arrhythmia by comparing the second change ratio with a second threshold, wherein
the first change ratio is a ratio of a difference between the interval and a previous interval to the previous interval,
the second change ratio is a ratio of a difference between the amplitude divided by the interval and a previous amplitude divided by the previous interval to the previous amplitude divided by the previous interval,
wherein the interval detection unit detects a maximum and a minimum of each pulse wave in a predetermined period along the time axis, calculates an internally dividing point between the maximum and the minimum at a predetermined ratio, detects a time at an intersecting point of the internally dividing point and each pulse wave, and calculates the interval as a difference between the time at the intersecting point and a time at a previous intersecting point, and
the amplitude detection unit calculates the amplitude as a difference between the maximum and the minimum.

2. The apparatus according to claim 1, wherein the predetermined ratio of the internally dividing point is above 0.64.

3. The apparatus according to claim 1, wherein the predetermined ratio of the internally dividing point is determined by a ratio of the maximum to a local maximum value in the pulse waves, measured previously.

4. The apparatus according to claim 1, wherein
the pulse waves detection unit differentiates the pulse waves along the time axis after detecting the pulse waves.

5. A method for measuring pulse waves, comprising:
detecting pulse waves of a subject;
detecting a plurality of amplitudes of the pulse waves;
detecting an interval of time between two of the pulse waves, the two being adjacent along a time axis;
calculating, using a processor, a first change ratio and a second change ratio, wherein
the first change ratio is a ratio of a difference between the interval and a previous interval to the previous interval,
the second change ratio is a ratio of a difference between the amplitude divided by the interval and a previous amplitude divided by the previous interval to the previous amplitude divided by the previous interval;
comparing the first change ratio with a first threshold; and
when the first change ratio is larger than the first threshold,
deciding whether the pulse waves represent arrhythmia by comparing the second change ratio with a second threshold,
wherein a step of detecting the interval includes
detecting a maximum and a minimum of the pulse waves in a predetermined period along the time axis;
calculating an internally dividing point between the maximum and the minimum at a predetermined ratio;
detecting a time at an intersecting point of the internally dividing point and the pulse waves; and
calculating the interval as a difference between the time at the intersecting point and a time at a previous intersecting point; and
a step of detecting the plurality of amplitudes includes calculating the amplitude as a difference between the maximum and the minimum.

\* \* \* \* \*